(12) United States Patent
Lu

(10) Patent No.: US 10,682,257 B2
(45) Date of Patent: Jun. 16, 2020

(54) BIOLOGICAL FIBER COMPOSITE DRESSING

(71) Applicant: HARVEST BELLE BIOTECH, New Taipei (TW)

(72) Inventor: Chi-Hsiang Lu, New Taipei (TW)

(73) Assignee: EVOPHANCIE BIOTECH LTD, New Taipei (TW)

( * ) Notice: Subject to any disclaimer, the term of this patent is extended or adjusted under 35 U.S.C. 154(b) by 1074 days.

(21) Appl. No.: 14/812,192

(22) Filed: Jul. 29, 2015

(65) Prior Publication Data

US 2017/0027759 A1 Feb. 2, 2017

(51) Int. Cl.
*A61F 13/00* (2006.01)
*A61L 15/44* (2006.01)
*A61L 15/40* (2006.01)

(52) U.S. Cl.
CPC .. *A61F 13/00012* (2013.01); *A61F 13/00017* (2013.01); *A61F 13/00029* (2013.01); *A61F 13/00063* (2013.01); *A61L 15/40* (2013.01); *A61L 15/44* (2013.01); *A61L 2300/22* (2013.01); *A61L 2300/254* (2013.01); *A61L 2300/414* (2013.01)

(58) Field of Classification Search
CPC .......... A61F 13/00012; A61F 13/00063; A61F 13/00029; A61F 13/00017; A61L 15/40; A61L 15/44; A61L 2300/414; A61L 2300/254; A61L 2300/22
See application file for complete search history.

(56) References Cited

U.S. PATENT DOCUMENTS

| | | | | |
|---|---|---|---|---|
| 4,378,431 A | * | 3/1983 | Brown, Jr. | ............... C12P 19/04 428/478.4 |
| 4,742,164 A | * | 5/1988 | Iguchi | ........................ C08L 1/02 264/207 |
| 5,144,021 A | | 9/1992 | Arie et al. | |
| 6,986,963 B2 | * | 1/2006 | Evans | ................. H01M 4/8605 429/2 |
| 2009/0209897 A1 | | 8/2009 | Limaye et al. | |
| 2010/0297239 A1 | * | 11/2010 | Gatenholm | ............. A61L 27/48 424/488 |
| 2011/0286948 A1 | * | 11/2011 | Lin | ........................ C12P 19/04 424/61 |
| 2013/0004784 A1 | | 1/2013 | Hessler et al. | |

FOREIGN PATENT DOCUMENTS

| | | |
|---|---|---|
| CN | 201949364 | 8/2011 |
| CN | 102533904 | 7/2012 |
| CN | 103083136 | 5/2013 |
| CN | 103481600 | 1/2014 |
| CN | 203694184 | 7/2014 |
| JP | 5-48947 | 6/1993 |
| JP | 5229063 | 9/1993 |
| JP | 2008-061532 | 3/2008 |
| JP | 2009-007721 | 1/2009 |
| JP | 2014-187901 | 10/2014 |
| TW | 201121588 | 7/2011 |

OTHER PUBLICATIONS

Shah, N et al. Effect of reactor surface on production of bacterial cellulose and water soluble oligosaccharides by Gluconacetobacter hansenii PJK. Biotechnology and Bioprocess Engineering. 2010. 15: 110-118. (Year: 2010).*
Watanabe, K et al. Structural features and properties of bacterial cellulose produced in agitated culture. Cellulose. 1998. 5: 187-200. (Year: 1998).*
Taiwanese Office Action for Taiwanese Patent Application No. 104102813 dated Feb. 2, 2016.
Chinese Office Action for Chinese Patent Application No. 201510046088.5 dated Feb. 4, 2017.
Japanese Office Action for Japanese Patent Application No. 2015-025333 dated Mar. 22, 2016.
Tajima, et al. "Cellulose synthesis with acetic acid bacteria and mass production of fermented nanocellulose", Apr. 10, 2014.
Extended European Search Report for European Patent Application No. 15178915.3 dated Dec. 3, 2015.

* cited by examiner

*Primary Examiner* — Susan E. Fernandez
(74) *Attorney, Agent, or Firm* — Amin, Turocy & Watson, LLP

(57) ABSTRACT

The present invention provides a biological fiber composite dressing. The biological fiber composite dressing includes: a cloth membrane having a first surface layer and an opposing second surface layer, wherein the cloth membrane has cloth membrane fibers; and a biological fiber membrane having a third surface layer and an opposing fourth surface layer, wherein the biological fiber membrane is formed by bacteria of the genus *Gluconacetobacter*, and the fourth surface layer is combined with the first surface layer, and a plurality of biological fibers being wound and combined with the cloth membrane fibers are extended along the fourth surface layer of the biological fiber membrane, such that the moisturizing effect of the dressing can be enhanced by the biological fiber membrane, thereby carrying more active ingredients.

14 Claims, 4 Drawing Sheets

BIOLOGICAL FIBER COMPOSITE DRESSING

BACKGROUND OF THE INVENTION

1. Field of the Invention

The present invention relates to biological fiber composite dressings, and more particularly, to a biological fiber composite dressing applied to the skin.

2. Description of the Related Art

In the current medical field, a cotton pad or gauze is mostly used as the dressing for the care of a wound. However, such type of dressing has some drawbacks, for example, a poor antibacterial property, a high possibility of a wound infection, easiness for developing wound adhesion, and difficulty to be removed.

Afterwards, the cotton pads and gauzes have been replaced with non-woven dressings, since the non-woven dressings have the characteristics of better absorbency and being capable of providing a moist environment to aid of the wound repair. However, when the liquid or moisture absorbed by the non-woven dressings is gradually reduced, the issue of wound adhesion is likely to arise.

On the other hand, in addition to the basic living requirements, the modern people pay more attention to cosmetic skin care, especially for the facial care. Hence, the beauty industry focuses on the demands of the facial care, and develops a variety of facial mask products. There are a variety of masks, such as a mud paste-type mask, a tear-peel type mask, a sheet-like mask, and so on.

Although the mud paste-type mask contains some ingredients or minerals for skin care, the mask has to be washed off after application. Hence, the ingredients for skin care are hard to be really absorbed by the skin. Further, because the mud paste-type mask contains more minerals, more preservatives must be added to prevent bacteria from growing in the moist mud paste. The tear-peel type mask has main ingredients, such as, polymer gel, water and alcohol, and promotes the blood circulation of the skin by increasing the epidermal temperature. However, since the tear-peel type mask is no peeled off until being dry, it might cause damage to the sensitive skin during the peeling of the mask. In addition, the tear-peel-type mask does not contain any moisturizing ingredients for the dryness of the mask, such that it is not appropriate for the dry skin. The sheet-like mask is a monolayer sheet absorbed with essence with specific functions, and it can be used for a variety of skin cares by adjusting the ingredients. Although the sheet-like mask does not need to be washed off after application, the mask does not have any cleaning effect. The above sheet-like mask is mostly made of a monolayer of non-woven fabric. For a user to apply the non-woven fabric soaked with the essence, a higher concentration of essence is required due to the rapid water evaporation in the non-woven fabric. Consequently, the essence is wasted, while the problem of water evaporation remains unresolved.

Therefore, the beauty industry has developed a biological fiber membrane as a mask. Although the biological fiber membrane has a better moisturizing property, the overall attaching comfort is poor. Besides, the entire sheet of the biological fiber membrane is not easy to expand after absorption with the essence. Thus, there is still a need to develop a novel dressing product.

SUMMARY OF THE INVENTION

In view of the above disadvantages of the prior art, the present invention provides a biological fiber composite dressing, including a cloth membrane having a first surface layer and an opposing second surface layer, wherein the cloth membrane has cloth membrane fibers; and a biological fiber membrane having a third surface layer and an opposing fourth surface, wherein the biological fiber membrane is formed by bacteria of the genus *Gluconacetobacter*, and the fourth surface layer is combined with the first surface layer, and the fourth surface layer has a plurality of biological fibers being wound and combined with the cloth membrane fibers extending therealong.

In one embodiment, the biological fiber membrane further has a three-dimensional reticular structure bound between the third surface layer and the fourth surface layer, wherein the density of the three-dimensional reticular structure is smaller than the density of the third surface layer and the fourth surface layer, and the three-dimensional reticular structure is extended to the interior of the first surface layer of the cloth membrane from the fourth surface, wherein the three-dimensional reticular structure is composed of a plurality of biological fibers.

Further, the three-dimensional reticular structure has a plurality of backbone fibers parallel to each other and a plurality of inter-layer fibers interwoven at any two of the adjacent backbone fibers. Both of the plurality of backbone fibers and the plurality of inter-layer fibers are biological fibers, and the diameter of each of the plurality of backbone fibers is greater than or equal to the diameter of each of the plurality of inter-layer fibers. Further, a plurality of backbone fibers are extended along a longitudinal direction or a width direction of the biological fiber membrane.

In yet one embodiment, the biological fiber composite dressing further includes an additional biological fiber membrane disposed on the second surface layer.

In another embodiment, the additional biological fiber membrane has a plurality of biological fibers being wound and combined with the biological fibers of the cloth membrane fibers.

The biological fiber composite dressing of the present invention has a cloth membrane and a biological fiber membrane, so as to enable the dressing to absorb more moisture or active ingredients by the biological fiber membrane. Since the biological fiber membrane has more delicate pores than the cloth membrane, it can prevent moisture from rapidly evaporating from the cloth membrane while having gas permeability, and thereby enhancing the moisturizing property of the dressing. Therefore, when the biological fiber composite dressing of the present invention is applied to the skin, for example, when it is used as a mask, the dressing does not need to absorb excess active ingredients. As a result, cost is saved substantially for the end-users.

BRIEF DESCRIPTION OF THE DRAWINGS

FIGS. 2A and 2B show scanning electron microscope (SEM) photographs of the biological fiber composite dressing of the present invention, wherein FIG. 2A shows a photograph of the three-dimensional reticular structure extended to the cloth membrane, and FIG. 2B shows a side view of the biological fiber membrane;

DETAILED DESCRIPTION OF THE PREFERRED EMBODIMENTS

Figure 1:
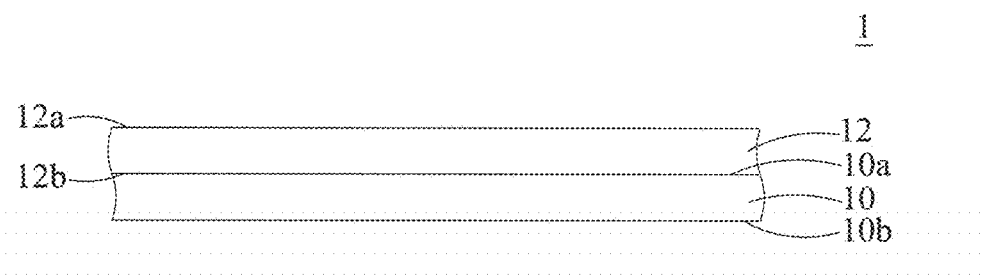
FIG. 1 is a schematic diagram of the structure of a biological fiber composite dressing of the present invention.

The following specific examples are used for illustrating the present invention. One skilled in the art can easily conceive the other advantages and effects of the present invention, from the disclosure of the present specification.

It should be noted that all of the drawings depict a structure, proportion, size, etc., are only used to match the specification for a person skilled in the art to understand and reads. It is not intended to limit the conditions which can be implemented in the present invention, such that it is not substantially meaningful technically. Any modification of the structure, change in the proportion or adjustment of the size are be within the scope encompassed in the technical contents disclosed in the present invention, without departing from the spirit of the present invention. At the same time, terms, such as "first," "second," "on" and "a/an" etc., are merely to facilitate the understanding of the descriptions, and should not be construed to limit the implemental scope of the present invention. Any change or adjustment of the relationships is also considered to be within the implemental scope, without any substantial changes to the technical content.

The term "parallel" used herein means the morphology of which a plurality of backbone fibers are in the same direction, such as a longitudinal direction or a width direction.

The present invention provides a biological fiber composite dressing, including a cloth membrane having a first surface and an opposing second surface, wherein the cloth membrane has cloth membrane fibers; and a biological fiber membrane having a third surface and an opposing fourth surface, wherein the biological fiber membrane is formed by bacteria of the genus *Gluconacetobacter*, and the fourth surface layer is combined with the first surface layer, and the fourth surface layer has a plurality of biological fibers being wound and combined with the cloth membrane fibers extending therealong.

The cloth membrane is a woven fabric or non-woven fabric. In general, the woven fabric is woven by textile technologies. The woven fabric is woven by using artificial fibers or natural fibers, or blending with the artificial fibers and the natural fibers. In a specific example, the artificial fibers are polyester, acrylics or nylon. The natural fibers are silk or cotton fibers.

The biological fiber membrane of the present invention is obtained by culturing microorganisms. It is found in the present invention that the biological fiber membrane formed by culturing bacteria of the genus *Gluconacetobacter* in a medium containing mannitol, peptone, yeast extract and agar has a plurality of biological fibers being wound and combined with the cloth membrane fibers.

In an embodiment for producing the biological fiber membrane, the fermentation of a strains takes place. First of all, a culture medium is provided in a container, and the culture medium contains some known components selected from gelatin, gum arabic, agar, and etc. The culture medium still needs some carbon sources, such as mannitol, glucose, and etc., and other components, such as peptone and yeast extract. The weight ratio of the carbon source, peptone and yeast extract is in a range from 5:1:1 to 4:1:1. Subsequently, the pH value of the culture medium is preferably controlled at acidic, such as between pH 0.5 to 6. The initial concentration of microorganisms can be controlled in a range of 102 to 105 bacteria/ml. The stationary culturing of the microorganisms is performed at 25 to 28° C. for 24 to 96 hours. Later, the aforesaid cloth membrane is placed flat in the culture medium. After 24 to 48 hours, a composite dressing is taken out, and the biological fiber composite dressing of the present invention is obtained.

After testing, the biological fiber membrane in the biological fiber composite dressing of the present invention has a plurality of biological fibers, and the amount of the biological fibers per unit area is from 0.005 g/cm$^2$ to 0.008 g/cm$^2$. The diameter of each of the biological fibers is from 20 nm to 100 nm.

In addition, after drying the biological fiber composite dressing of the present invention and then re-absorbing water and active ingredients, the biological fiber composite dressing has at least 50% of rehydration rate, at least 60% of rehydration rate, at least 70% of rehydration rate, even up to 91% of rehydration rate. In another aspect, the thickness of the biological fiber membrane of the biological fiber composite dressing is at least 20 μm, such as from 20 μm to 30 μm, or from 20 μm to 26 μm, or from 24 μm to 26 μm.

As shown in FIG. 1, a biological fiber composite dressing 1 of the present invention includes a cloth membrane 10 having a first surface layer 10a and an opposing second surface layer 10b; and a biological fiber membrane 12 disposed on the first surface layer 10a. The biological fiber membrane 12 has a third surface layer 12a and a fourth surface layer 12b, and the fourth surface layer 12b is combined with the first surface 10a.

Figure 2A:
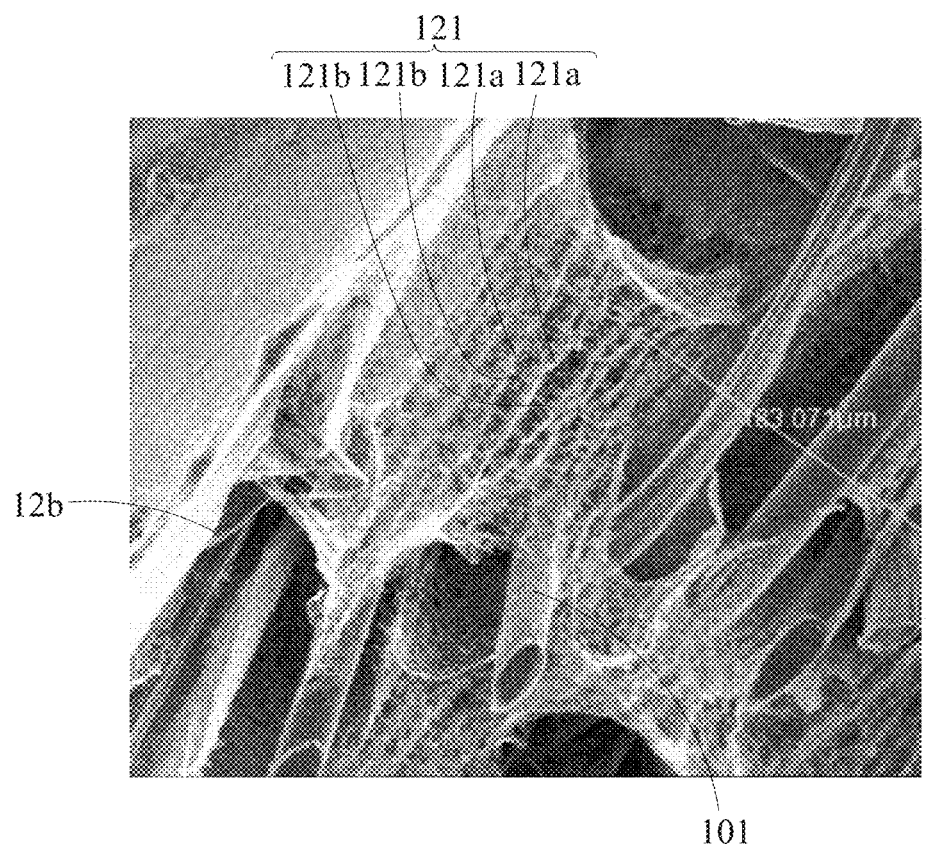

In addition, as shown in FIG. 2A, a plurality of biological fibers being wound and combined with the cloth membrane fibers 101 are extended along the fourth surface layer 12b of the biological fiber membrane 12.

As shown in FIG. 2A, the biological fiber membrane 12 has a three-dimensional reticular structure 121, and is extended to the interior of the first surface layer 10a of the cloth membrane 10 from the fourth surface layer 12b. The three-dimensional reticular structure 121 is composed of a plurality of biological fibers. More particularly, the three-dimensional reticular structure 121 has a plurality of backbone fibers 121a parallel to each other and a plurality of inter-layer fibers 121b interwoven at any two of the adjacent backbone fibers 121a. Therefore, any two of the adjacent backbone fibers 121a are linked in the horizontal and vertical directions, to form the three-dimensional reticular structure 121. Both of the backbone fibers 121a and the inter-layer fibers 121b are biological fibers. As shown in FIG. 2A, the diameter of each of the backbone fibers 121a is greater than or equal to the diameter of each of the inter-layer fibers 121b. Even, it can be found that the diameter of each of the backbone fibers 121a is smaller than the diameter of each of the cloth membrane fibers 101.

Figure 2B:
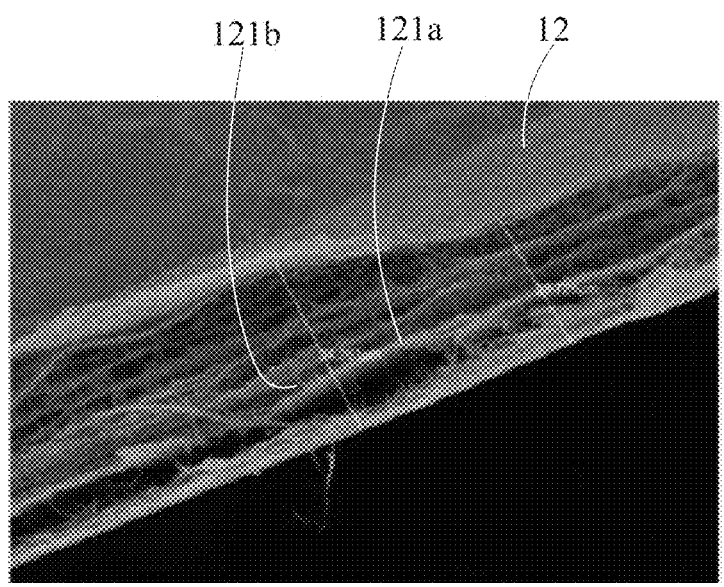

As shown in FIG. 2B, a side view of the biological fiber membrane 12 is provided, wherein the biological fiber membrane 12 also has a plurality of backbone fibers 121a, which are parallel to each other or extended along a longitudinal direction or a width direction of the biological fiber membrane 12, and a plurality of inter-layer fibers 121b interwoven with the backbone fibers 121a. Besides, the three-dimensional reticular structure is bound between two surface layers of the biological fiber membrane 12. The density of the three-dimensional reticular structure is smaller than the density of the two surface layers, for example, the density of the third surface and the fourth surface layer. In this example, the thickness of the biological fiber membrane of the biological fiber composite dressing is from 20 µm to 30 µm.

Figure 3A:
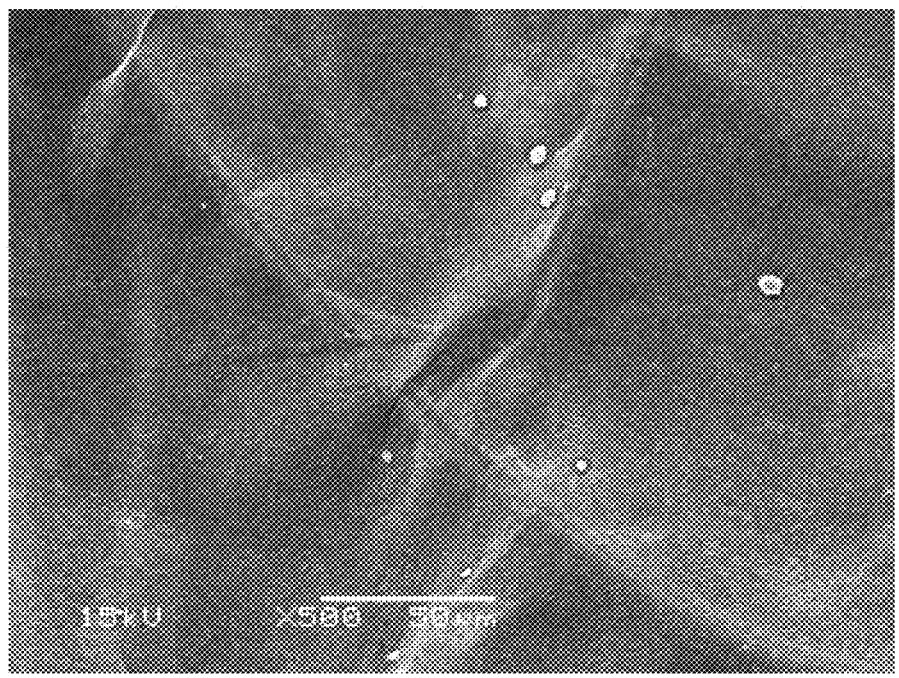
FIGS. 3A and 3B show an SEM photograph taken at 500× magnification of the biological fiber membrane side of the biological fiber composite dressing of the present invention and an SEM photograph at 500× magnification of a conventional biological fiber membrane, respectively.
Figure 3B:
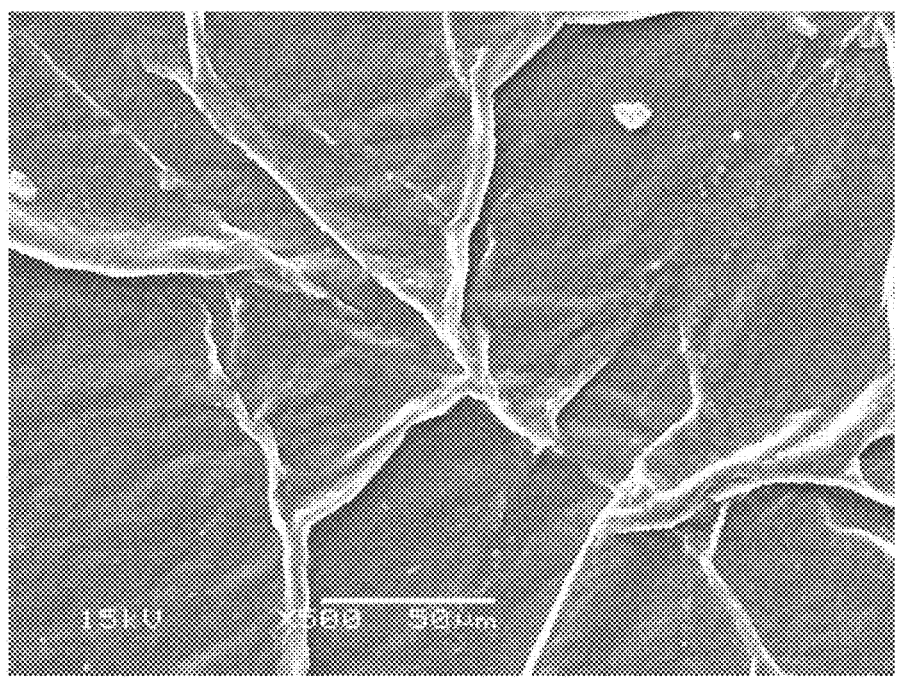

As shown in FIGS. 3A and 3B, an SEM photograph at 500× magnification of the biological fiber membrane side of the biological fiber composite dressing of the present invention and a SEM photograph at 500× magnification of the conventional biological fiber membrane, respectively, are provided.

As shown in FIG. 3A, the biological fiber membrane side of the biological fiber composite dressing of the present invention is flat. The strips shown in FIG. 3A are the cloth membrane fibers underneath the biological fiber membrane. Hence, the biological fiber membrane side of the biological fiber composite dressing of the present invention is very flat. On the contrary, the surface of the conventional biological fiber membrane shown in FIG. 3B has many foldings. Therefore, poor attachment of such biological fiber membrane to the skin affects touch, and also results in poor absorbency of drugs or active ingredients.

Figure 4:
FIG. 4 shows a schematic diagram of the biological fiber composite dressing of the present invention having an additional biological fiber membrane.

As shown in FIG. 4, if the cloth membrane 20 is provided in the container for a longer period during culturing or the cloth membrane 20 is flipped over, an additional biological fiber membrane 22' is formed on the second surface layer 20b of the cloth membrane 20. In this example, in addition to the biological fiber membrane 22 formed on the first surface layer 20a, an additional biological fiber membrane 22' is further included.

The biological fiber composite dressing of the present invention is provided to apply to the skin. It is particularly useful as a mask. Thus, the biological fiber composite dressing of the present invention can further includes an active ingredient or a drug. The examples of the active ingredient include humectants, whitening ingredients, anti-wrinkle ingredients, exfoliating ingredients, growth factors and enzymes. Additions of different active ingredients enable the biological fiber composite dressing of the present invention to have the effects for stress relief and body massage.

A Tensile Strength Test on the Biological Fiber Composite Dressing of the Present Invention The biological fiber composite dressing of the present invention was cut into test pieces each with a size of 15 mm×15 mm, and then three test pieces were subjected to a tensile strength test. The obtained results were 2113.70 g/15 mm, 2145.00 g/15 mm and 1951.90 g/15 mm, respectively. The average value of the tensile strength is 2070.20 g/15 mm.

The conventional biological fiber membrane was subjected to the same test, and its tensile strength was up to 2607.33 g/15 mm. It can be seen that the biological fiber composite dressing of the present invention has better pliability than the conventional biological fiber membrane.

An Elongation Test on the Biological Fiber Composite Dressing of the Present Invention In addition, the biological fiber composite dressing of the present invention was subjected to an elongation test, and the obtained results were 21.00%, 16.20% and 16.60%, respectively. The average value of the elongation was 17.93%. The conventional biological fiber membrane was subjected to the same test, but its elongation was only 5.66%. It is thus clear that the elongation for the biological fiber composite dressing of the present invention is significantly better, and the biological fiber composite dressing can be extended and attached to a larger area.

A Water Absorbency Test on the Biological Fiber Composite Dressing of the Present Invention Three test pieces, each with a dimension of 100 mm×15 mm, were subjected to a water absorbency test. First, deionized water was injected in a dish, and kept the water temperature at 23±° C. Then, the test pieces were contacted with water to measure a water absorption height for one minute.

The results show that the average height of the water absorption for the biological fiber composite dressing of the present invention was 40 mm, while the average height for the conventional biological fiber membrane was 1 mm. Thus, the biological fiber composite dressing of the present invention has better water absorbency.

Measurements for the Amount of the Biological Fibers Per Unit Area in the Biological Fiber Composite Dressing of the Present Invention The biological fiber composite dressing of the present invention was cut into 16 pieces, each with a size of 5 cm×5 cm. The pieces were dried at 60° C. for 10 minutes, and then weighed for their dry weights. The dry weight of each of the pieces after deducting the dry weight of the cloth membrane was divided by area of the piece. The obtained amounts of the biological fibers per unit area were from 0.005 g/cm$^2$ to 0.008 g/cm$^2$.

In comparison, the amount of the biological fibers per unit area of the conventional biological fiber membrane was only 0.001 g/cm$^2$.

A Rehydration Rate Test of the Biological Fiber Composite Dressing of the Present Invention The wet weights of the biological fiber composite dressing of the present invention and the conventional biological fiber membrane were measured. Then, the dressing and the biological fiber membrane were dried at 20° C. for 30 minutes. After the dressing and the biological fiber membrane were curly, white and filamentous, the dry weights were measured. Subsequently, the dressing and the biological fiber membrane were contacted with water for 30 minutes, and the weights after rehydration were recorded. The rehydration rate was obtained by dividing the weight after rehydration by the weight difference between the wet weight and the dry weight.

It was found that the biological fiber composite dressing of the present invention had a rehydration rate of at least 50%, and at most 91%. By contrast, the conventional biological fiber membrane could not absorb water. The reason was that the amount of the biological fibers per unit area in the conventional biological fiber membrane was only 0.001 g/cm$^2$, while the amount of the biological fibers per unit area in the biological fiber membrane of the biological fiber composite dressing of the present invention was from 0.005 g/cm$^2$ to 0.008 g/cm$^2$. Thus, the biological fiber composite dressing of the present invention has an excellent rehydration rate.

Permeability Test on the Biological Fiber Composite Dressing of the Present Invention The biological fiber composite dressing of the present invention and the conventional biological fiber membrane were placed flat, on a substrate, and then the same amount of stained essences was added onto the biological fiber composite dressing of the present invention and the conventional biological fiber membrane, respectively. After 10 seconds, the permeability of the substrate was observed visually.

Figure 5:
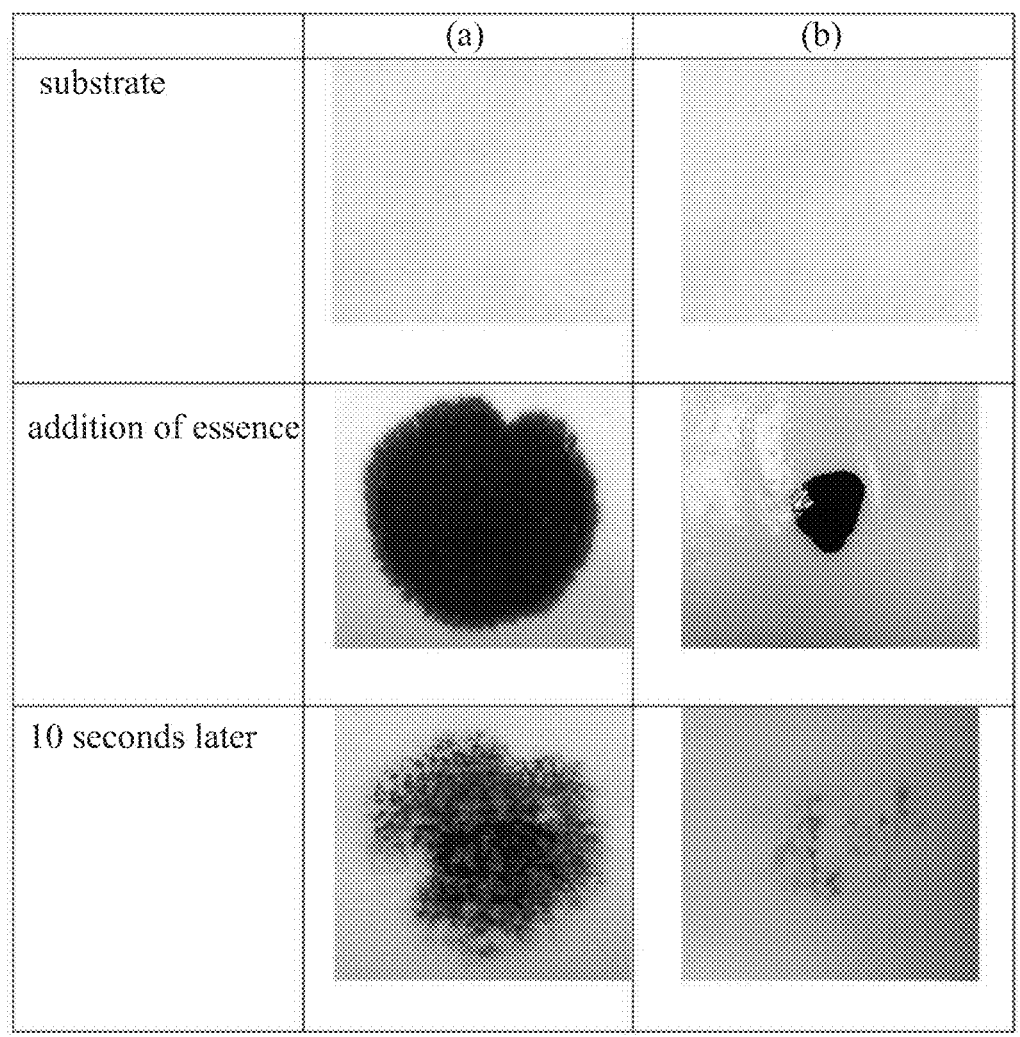
FIG. 5 is a chart showing the results of a permeability test on the biological fiber composite dressing of the present invention and the conventional biological fiber membrane, wherein Column A shows the test result of the biological fiber composite dressing of the present invention, and Column B shows the test result of the conventional biological fiber membrane.

As shown in FIG. 5, Column A shows the test result of the biological fiber composite dressing of the present invention, and Column B shows the test result of the conventional biological fiber membrane. Among these results, when the essences were just added onto the conventional biological fiber membrane, the essences had poor spreading. After 10 seconds, the essences could not penetrate effectively thorough the substrate. By contrast, the biological fiber composite dressing of the present invention had better diffusibility and significant permeability.

In summary, the biological fiber composite dressing of the present invention includes a cloth membrane and a biological fiber membrane, so as to enable the biological fiber membrane to absorb more moisture or active ingredients. Since the biological fiber membrane has more delicate pores than the cloth membrane, it can prevent moisture from rapidly evaporating from the cloth membrane while having gas permeability, and thereby enhancing the moisturizing property of the dressing. In another aspect, when one side of the biological fiber composite dressing of the present invention is the cloth membrane, the dressing has an attaching comfort and a long-lasting moisturizing property at the same time. Therefore, when the biological fiber composite dressing of the present invention is applied to the skin, for example, when it is used as a mask, the dressing does not need to absorb excess active ingredients. As a result, the cost is saved substantially for the end-users.

While the examples are used to illustrate the principle of the present invention and the effect being brought about, they are not intended to limit the preset invention. Any one skilled in the art can make modifications to the examples above without substantially departing from the spirit and scope of the present invention. Therefore, the scope of the present invention should be accorded to the appended claims.

What is claimed is:

1. A biological fiber composite dressing, comprising:
    a cloth membrane having a first surface layer and an opposing second surface layer, wherein the cloth membrane comprises cloth membrane fibers; and
    a biological fiber membrane formed by stationary culturing bacteria of the genus *Gluconacetobacter* in a culture medium containing gelatin, gum arabic, or agar, wherein the biological fiber membrane has a third surface layer and an opposing fourth surface layer, and wherein the fourth surface layer is combined with the first surface layer, and the fourth surface layer comprises a plurality of biological fibers being wound and combined with the cloth membrane fibers extending therealong,
    wherein the biological fiber membrane further comprises a three-dimensional reticular structure bound between the third surface layer and the fourth surface layer, and wherein the three-dimensional reticular structure extends to the interior of the first surface layer of the cloth membrane from the fourth surface layer, and the three-dimensional reticular structure has a plurality of backbone fibers parallel to each other and a plurality of inter-layer fibers interwoven at any two of adjacent backbone fibers, the plurality of backbone fibers extend along a longitudinal direction or a width direction of the biological fiber membrane, and the amount of the biological fibers of the biological fiber membrane per unit area is from 0.005 $g/cm^2$ to 0.008 $g/cm^2$, and the diameter of each of the biological fiber is from 20 nm to 100 nm, and the biological fiber composite dressing has a rehydration rate of at least 50%.

2. The biological fiber composite dressing of claim 1, wherein the three-dimensional reticular structure is composed of the plurality of biological fibers.

3. The biological fiber composite dressing of claim 1, wherein the cloth membrane is a woven fabric, and wherein the woven fabric is woven by using an artificial fiber or a natural fiber, or blended with the artificial fiber and the natural fiber.

4. The biological fiber composite dressing of claim 3, wherein the artificial fiber is selected from the group consisting of polyester, acrylics and nylon.

5. The biological fiber composite dressing of claim 3, wherein the natural fiber is one of silk and a cotton fiber.

6. The biological fiber composite dressing of claim 1, wherein the cloth membrane is a non-woven fabric.

7. The biological fiber composite dressing of claim 1, further comprising an additional biological fiber membrane disposed on the second surface layer.

8. The biological fiber composite dressing of claim 7, wherein the additional biological fiber membrane has a plurality of biological fibers being wound and combined with the cloth membrane fibers.

9. The biological fiber composite dressing of claim 1, further comprising an active ingredient or a drug.

10. The biological fiber composite dressing of claim 9, wherein the active ingredient is selected from the group consisting of a humectant, a whitening ingredient, an anti-wrinkle ingredient, an exfoliating ingredient, a growth factor, and an enzyme.

11. The biological fiber composite dressing of claim 1, wherein the biological fiber membrane is formed by stationary culturing the bacteria of the genus *Gluconacetobacter* in a culture medium having mannitol, peptone, yeast extract, and agar.

12. The biological fiber composite dressing of claim 1 having a rehydration rate of 50% to 91%.

13. The biological fiber composite dressing of claim 1, wherein a thickness of the biological fiber membrane is at least 20 μm.

14. The biological fiber composite dressing of claim 13, wherein the thickness of the biological fiber membrane is from 20 μm to 30 μm.

* * * * *